United States Patent [19]

Smith

[11] 3,975,825
[45] Aug. 24, 1976

[54] ORTHO-ACTIVATING METHOD AND APPARATUS

[76] Inventor: C. Perry Smith, 2893 Grove Lane, Ventura, Calif. 93003

[22] Filed: June 11, 1975

[21] Appl. No.: 585,776

[52] U.S. Cl. ................................ 32/14 R; 32/14 A
[51] Int. Cl.² ........................................ A61C 7/00
[58] Field of Search ............... 32/14 R, 14 A, 14 B, 32/14 C, 14 E, 2

[56] References Cited
UNITED STATES PATENTS

| | | | |
|---|---|---|---|
| 1,582,570 | 4/1926 | Brust | 32/14 E |
| 2,266,860 | 12/1941 | Griesinger | 32/14 E |
| 3,162,948 | 12/1964 | Gerber | 32/14 E |
| 3,284,902 | 11/1966 | Dellberg et al. | 32/14 E |
| 3,827,146 | 8/1974 | Wallsheim | 32/14 E |

*Primary Examiner*—Jack Q. Lever
*Attorney, Agent, or Firm*—Ralph B. Pastoriza

[57] ABSTRACT

A removable orthodontic appliance for moving teeth is provided. It includes at least one or more inflatable membranes that are incorporated into the basic framework of the appliance. These inflatable membranes are inflated to desired pressures and the appliance is placed in the mouth so that the inflated membrane is on the opposite side of the direction the tooth is to be moved.

8 Claims, 4 Drawing Figures

ORTHO-ACTIVATING METHOD AND APPARATUS

This invention relates to a new method and apparatus for moving teeth to a more esthetic and/or functional position within the dental arch.

BACKGROUND OF THE INVENTION

Conventionally, teeth are straightened by applying pressure, usually with wire springs, secured to an appliance inserted in the patient's mouth. The wire springs themselves generally make a point or line contact with the tooth, and if proper movement of the tooth is to follow, the point of application of the force can become somewhat critical.

Another conventional method is to band the teeth individually, then by using resilient wires attached to prewelded brackets on the bands, the teeth are moved into proper alignment. A major disadvantage of this is that: 1) the teeth are not permitted free physiological movement and, 2) expansion of the dental arch is difficult to achieve.

While such orthodontic treatment has been generally effective, with springs, elastics and wires, there is not only discomfort in the mouth, but in addition food particles and the like can easily become entrained in the wire mechanisms.

BRIEF DESCRIPTION OF THE PRESENT INVENTION

With the foregoing in mind, the present invention supplies a different and additional force concept to the conventional orthodontic methods. More particularly, rather than employ spring wires, rubber bands, and the like, for exerting a force or pressure against a tooth or teeth to be moved, a pneumatic system is provided. The teeth, with this method, remain free in their physiological environment. Since the force is directed generally in a lingual to labial direction, arch expansion is possible.

Essentially, and in accord with the method of this invention, a basic framework is designed to define a chamber having a front opening adjacent to the tooth to be straightened when positioned in the mouth. An inflatable membrane is inserted into the chamber and thereafter inflated to a given pneumatic pressure. The framework is then inserted on the patient's teeth such that the inflated membrane exerts a pressure through the front opening of the chamber on the tooth, the basic framework itself holding the chamber in a stationary position relative to the patient's dentition.

In the event several teeth require movement, the basic framework may include additional chambers or one enlarged chamber with front opening lingual to the additional teeth involved. Individual additional inflatable membranes are provided for the additional chambers respectively and inflated at various pressures to provide the desired pressure or force on the additional teeth as dictated by the position of the teeth.

The basic framework can be periodically removed and pressure replenished in the individual inflatable membranes as required. This appliance, of course, can also be removed by the patient for the purpose of cleaning.

The foregoing method and appropriate apparatus for carrying out the method results in a fairly compact appliance which does not include extending wires or deep crevices which could trap food particles and the like. Moreover, the appliance itself is relatively comfortable for the patient to wear and the provision of pneumatic pressure results in application of force over a fairly substantial area of the tooth.

BRIEF DESCRIPTION OF THE DRAWINGS

A better understanding of this invention will be had by referring to the accompanying drawings in which.

DETAILED DESCRIPTION OF THE INVENTION

Figure 1:
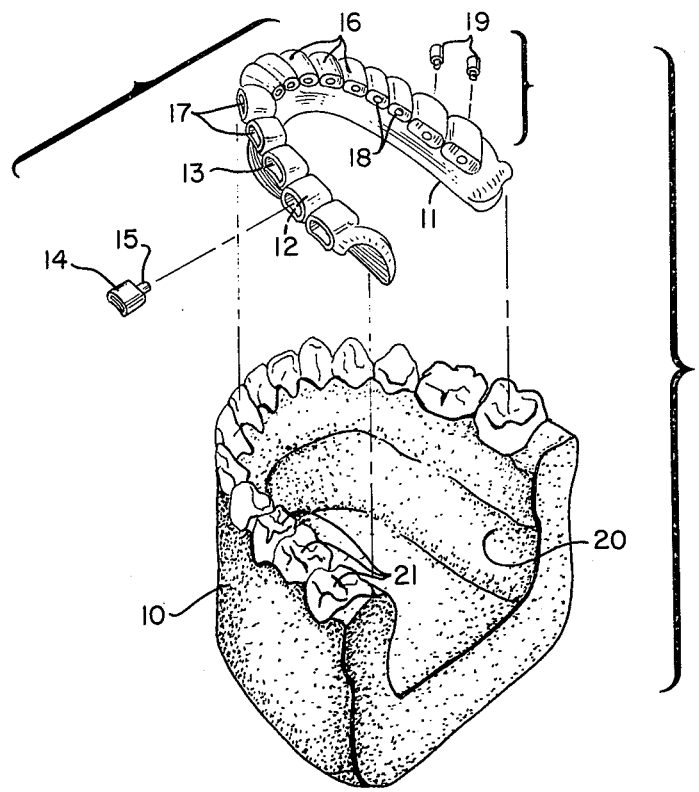
FIG. 1 is a perspective view of a cast of a patient's lower arch and teeth showing in exploded view the basic framework pneumatically controlled appliance of this invention.

Referring first to FIG. 1 there is shown a cast 10 of a patient's arch and teeth which might, for example, be the lower arch. In exploded view above the cast 10 is shown the basic framework 11 constituting the appliance of the present invention employed for straightening the patient's teeth.

With particular reference to the basic framework 11, the same is made from the cast 10 by a molding operation so as to fit the patient's arch comfortably with portions of the basic framework generally lingual to the teeth. The framework 11 will thus hold itself in a fixed position relative to the patient's jaw when inserted.

In accord with a feature of the invention, the basic framework includes at least one chamber 12 having a front opening 13 generally lingual to a tooth to be straightened when the basic framework is positioned on the patient's teeth.

Shown exploded from the chamber 12 is an inflatable membrane 14 receivable in the front opening 13 and including a rear air inlet 15 arranged to pass through the rear wall of the chamber. The arrangement is such that the inflatable membrane 14 when positioned within the chamber can be inflated from the rear with air to a given pressure so that when the basic framework 11 is positioned on the patient's teeth, the inflatable membrane will exert a pressure against the lingual area of the patient's tooth through the front opening of the chamber.

In the particular embodiment illustrated in FIG. 1, the basic framework includes additional chambers 16 having front openings 17 and individual rear air inlets 18. These additional chambers are arranged to receive additional inflatable membranes such as indicated in exploded view at 19, the additional inflatable membranes being inflated with air to various pressures through the air inlet portions passing through the rear air inlets 18. The particular pressures are dictated by the position of the particular teeth adjacent to the membranes at the front openings of the associated chambers when the basic framework is inserted in the patient's mouth.

With the foregoing arrangement, several teeth can be straightened simultaneously, all having various pressures applied as required.

The basic framework 11 itself includes lower portions arranged to snugly engage about the upper arch 20 of the cast 10 and thus about the arch 20 of the patient's teeth. For convenience, the teeth on the cast 10 which are identically positioned to the patient's teeth are designated by the numeral 21 as are also the patient's teeth in the further description of the use of the appliance.

Figure 2:
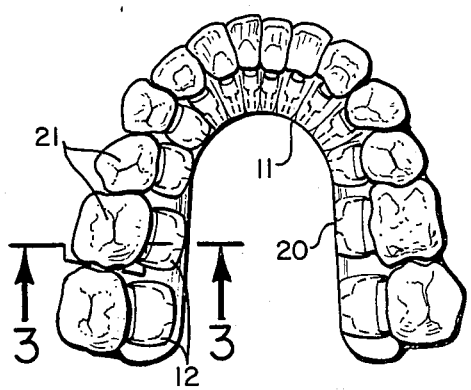
FIG. 2 is a plan view of the appliance in position on a patient's teeth.

Thus, referring to FIG. 2, the appliance in the form of the basic framework 11 is shown over the arch 20 with the front openings of the various chambers such as the chamber 12 lingual to a patient's tooth such as 21 to be moved.

Figure 3:
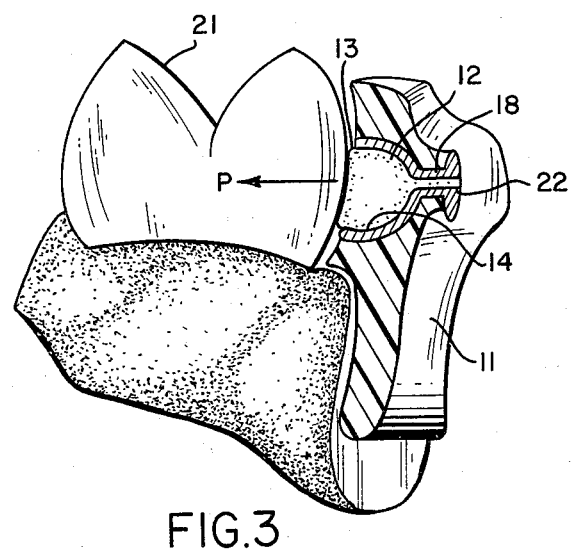
FIG. 3 is a greatly enlarged view of one tooth in the patient's mouth showing the basic framework appliance in cross section taken generally in the direction of the arrows 3—3 of FIG. 2; and, FIG. 4 is an enlarged perspective view of a metal casing illustrating one manner of defining suitable pneumatic chambers in the basic framework.

With particular reference to FIG. 3, further details of the basic framework, chamber and inflatable membrane structure of the device described in FIGS. 1 and 2 will be evident. As shown, the inflatable membrane 14 has a rear inlet portion which extends through the air inlet passage 18 to the chamber 12. The front portion of the inflatable membrane facing the tooth 21 has an area substantially co-extensive with the area of the front opening 13 of the chamber 12 and in actual practice will engage at least ten per cent of the adjacent tooth area so that the force tending to move the tooth due to the pneumatic pressure is exerted over a fairly substantial area of the tooth. The direction of the force or pressure is indicated by the arrow P in FIG. 3.

In the particular structure illustrated in FIG. 3, the cavity 12 may be formed by inserting suitable dies shaped as desired for the cavities and molding the basic framework about these dies and thence removing the dies to leave simply the cavity. The membrane can then be inserted in the cavity with its air inlet portion exiting out the rear opening 18 of the cavity. The constriction is sufficient that upon inflating the membrane, the pneumatic pressure will hold the outlet portion closed so that air cannot escape. In this respect, the inflation could be done by a hypodermic needle type of one-way valve or self sealant substance could be incorporated such as that used for basketballs or footballs which require the insertion of a thin, hollow tube having an end opening for inflation but upon withdrawal result in a pneumatic seal.

Figure 4:
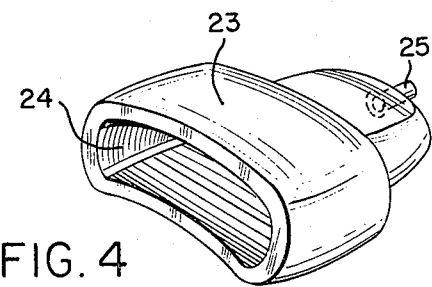

FIG. 4 illustrates a modified embodiment of the invention wherein the chambers are defined by a metal casing 23 having a front opening 24 with a rear air passage 25. In this instance, the various metal casings may be properly held in a position and the basic framework molded about the casings, the casings themselves becoming a permanent part of the appliance. The material of the appliance itself can be metal or plastic, the molding thereof being effected on the cast 10 shown in FIG. 1.

It will be appreciated from the view of FIG. 4 that the area of the front opening 24 is sufficient such that the membrane will bear against a substantial area of the tooth.

OPERATION

In operation, after the basic framework has been prepared by molding the same from a cast of the patient's teeth, the various membranes may be inserted in one or more of the chambers and inflated as by a hypodermic needle through the rear air inlet openings to desired pneumatic pressures. The appliance is then fitted in the patient's mouth on his teeth so that the membranes will exert the desired pneumatic force against the tooth or teeth to be moved.

Periodically, the basic framework may readily be removed and the inflatable membranes further inflated or even deflated in certain instances in accordance with the progress of tooth movement.

It will be appreciated from the foregoing description that a unique and useful method and apparatus for straightening teeth are provided by the present invention. Not only is the basic framework incorporating the chambers and inflatable membranes more comfortable for a patient to wear and less subject to the catching of food particles and the like, but in addition individual pressures against individual teeth can be carefully controlled. Moreover, the pressure is applied over a fairly large area of the tooth as described and thus enables movement of the tooth in a uniform and accurate manner without damaging the tooth surface itself.

It should be understood that while the procedure has been described as inflating the membranes prior to insertion of the basic framework in the patient's mouth, it is possible to inflate individual membranes while the basic framework appliance is actually on the patient's teeth by utilizing a simple hypodermic needle and simply inserting the same through the various air inlet openings as required. Since the basic framework is easily removable and insertable, however, the normal procedure would be to inflate the various membranes exterior of the patient's mouth.

From the foregoing description, it will be evident that the present invention has provided a greatly improved method and ortho-activating apparatus overcoming various problems associated with prior art methods and appliances.

What is claimed is:
1. A method of exerting pressure on a patient's tooth in an orthodontic treatment for moving teeth comprising the steps of:
   a. providing a base framework from molds of the patient's teeth wherein said base framework defines a chamber having a front opening adjacent to the tooth to be moved when positioned in the mouth;
   b. inserting an inflatable membrane in the chamber;
   c. inflating said membrane to a given pneumatic pressure; and,
   d. inserting said framework on the patient's teeth, whereby the inflated membrane exerts a pressure through said front opening on said tooth, said basic framework holding said chamber in a stationary position relative to the patient's jaw.

2. The method of claim 1, including the additional steps of defining additional chambers in said basic framework having front openings adjacent to additional teeth to be straightened when positioned in the mouth; inserting additional inflatable members in said additional chambers respectively; inflating said additional membranes to given pressures in accordance with the degree of movement required for said additional teeth prior to insertion of said framework in the patient's mouth, whereby additional teeth have pressures exerted thereon to move the same simultaneously with the pressure exerted on said first mentioned tooth.

3. The method of claim 1, in which said basic framework is periodically removed and pressure in said membrane changed by further inflation or deflation in accordance with the progress being made in moving said tooth to straighten the same.

4. The method of claim 1, in which said front opening has an area at least equal to ten per cent of the rear surface area of the tooth so that the force supplied by pneumatic pressure is distributed over an appreciable area of the tooth.

5. An ortho-activating apparatus comprising, in combination:
   a. a basic framework receivable in a patient's mouth and conforming to the patient's arch so that the framework is generally lingual to the teeth and holds itself in a fixed position relative to the patient's jaw, said basic framework including at least one chamber having a front opening lingual to a tooth to be moved; and,
   b. an inflatable membrane receivable in said chamber and having an air inlet portion passing through the rear of said chamber for receiving air under pressure so that said membrane can be inflated to a given pressure, whereby a pneumatic uniform force is applied by said membrane through said front opening over an area of the tooth to thereby provide a uniform pressure against the tooth to gradually move said tooth.

6. An apparatus according to claim 5, in which said basic framework includes additional chambers having front openings generally lingual to additional teeth to be straightened; and additional inflatable membranes receivable in said additional chambers respectively, each having an individual air inlet portion passing through the rear of its associated chamber for receiving air under pressure, so that each membrane may be inflated to a desired pressure as dictated by the position of the particular tooth lingual to the membrane at the front opening of the associated chamber, whereby various pressures may be exerted against various teeth simultaneously when said base framework is positioned in the patient's mouth.

7. An apparatus according to claim 5, in which said chamber is defined by a metal casing about which said basic framework is molded, said casing having a rear tubular portion defining a passage for said air inlet portion.

8. An apparatus according to claim 5, in which said front opening has an area at least equal to ten per cent of the rear surface area of the tooth whereby force is applied to the tooth over an appreciable area.

* * * * *